United States Patent
Inoue et al.

(10) Patent No.: US 6,473,642 B1
(45) Date of Patent: Oct. 29, 2002

(54) DIVIDABLE TYPE APPARATUS FOR MEASURING LIVING BODY IMPEDANCE

(75) Inventors: Koki Inoue, Niiza; Yoshinori Fukuda, Akita, both of (JP)

(73) Assignee: Tanita Corporation, Tokyo (JP)

(*) Notice: Subject to any disclaimer, the term of this patent is extended or adjusted under 35 U.S.C. 154(b) by 33 days.

(21) Appl. No.: 09/697,720

(22) Filed: Oct. 27, 2000

(30) Foreign Application Priority Data

Oct. 27, 1999 (JP) .......................... 11-305751
Aug. 28, 2000 (JP) ........................ 2000-256813

(51) Int. Cl.⁷ ............................................. A61B 5/05
(52) U.S. Cl. ................................................. 600/547
(58) Field of Search ........................ 600/547, 300, 600/301, 306, 372, 386, 348, 548

(56) References Cited

U.S. PATENT DOCUMENTS

| | | | | |
|---|---|---|---|---|
| 5,333,618 A | * | 8/1994 | Lekhtman et al. | 600/547 |
| 5,579,782 A | * | 12/1996 | Masuo | 600/547 |
| 6,067,468 A | * | 5/2000 | Korenman et al. | 600/547 |
| 6,088,615 A | * | 7/2000 | Masuo | 600/547 |
| 6,188,925 B1 | * | 2/2001 | Kawanishi et al. | 600/547 |
| 6,308,096 B1 | * | 10/2001 | Masuo | 600/547 |

FOREIGN PATENT DOCUMENTS

| | | |
|---|---|---|
| JP | 11-19059 | 1/1999 |
| JP | 11-113871 | 4/1999 |
| JP | 11-244252 | 9/1999 |

* cited by examiner

*Primary Examiner*—Kevin Shaver
*Assistant Examiner*—Navin Natnithithadha
(74) *Attorney, Agent, or Firm*—McDermott, Will & Emery

(57) ABSTRACT

Disclosed is a dividable apparatus for measuring living body impedance in which a first housing section 22 having a first current feeding electrode 4 and a first measurement electrode 5 mounted thereon can be physically separated from a second housing section 3 having a second current feeding electrode 6 and a second measurement electrode 7 mounted thereon, but said first and second housing sections 22, 3 are kept electrically connected to each other via an electric cable 11, whereby said first and second housing sections 22, 3 can freely be positioned on any parts of the body for impedance measurement.

8 Claims, 4 Drawing Sheets

DIVIDABLE TYPE APPARATUS FOR MEASURING LIVING BODY IMPEDANCE

BACKGROUND OF THE INVENTION

1. Field of the Invention

The present invention relates to an apparatus for measuring living body impedance for a person and for producing information effective for health care such as body fat percentage, amount of body water and the like. More particularly the present invention relates to a living body impedance measuring apparatus comprising a dividable housing that can be divided into two housing sections for freely setting the distance between the electrodes mounted thereon.

2. Description of the Prior Art

In the past, various types of body fat measuring apparatus, known as a kind of living body impedance measuring apparatus, have been proposed for measuring the living body impedance and for producing corpulence information such as body fat percentage that is a factor indicating a possibility for adult noncommunicable disease.

Among those, one typical apparatus currently available is a compact type body fat measuring apparatus. This compact type measuring apparatus comprises a measuring means, an arithmetic means, an input means and a display means enclosed within a housing, and several current feeding and measuring electrodes mounted on a front and a rear sides of the housing. Also known in the art and has been put into the market before said compact type apparatus is such body fat measuring apparatus that includes an integral weight meter and measures the impedance between both feet of a person. In addition, a body fat measuring apparatus that measures the impedance between both hands of a person while grasping a handle with both hands has also been known in the art before said compact type apparatus. However, those body fat measuring apparatus known in the art before said compact type apparatus are only effective for measuring the impedance between predetermined parts of a human body. In contrast thereto, said compact type body fat measuring apparatus is significantly advantageous in that it can measure the impedance between one of the hands and any one of the parts of the human body. (Refer to TOKUKAIHEI No.11-19059.)

However, said compact type body fat measuring apparatus suffers from such problem that, because of the fact that a person under test must act also as an operator for the apparatus, it is difficult for a handicapped person such as a patient keeping in bed to perform the measurement.

In addition, even in case of a normal person, to measure the impedance between one of the hands and one of the feet, for example, the person must take an unnatural pose, such as to bend his body, which causes an additional burden to the person. This may also produce an unstable condition for muscle and fat in the body, resulting in erroneous measurement.

Furthermore, because of the construction in which one of the hands must be used as a reference, the compact type measuring apparatus can not handle such case that the measurement should be performed between any two points on an abdominal region of the person for estimating body fat percentage.

The compact type measuring apparatus is also defective in that during the time for measuring the impedance between one of the hands and an abdomen of the person the person can not monitor the progress of measurement because of a display unit directed outside the view field of the person.

Furthermore, because of the measurement performed between one of the hands and any one of the parts of the body, rather than between predetermined parts such as both feet and both hands, the person can not see what part of the body is now being measured by the apparatus. It may happen that the person misunderstands the part of the body for measurement.

In view of the above an object of the present invention is to provide a new and improved living body impedance measuring apparatus that can solve the problems of the prior art compact type body fat measuring apparatus, as described above.

SUMMARY OF THE INVENTION

In order to achieve such object the present invention provides a dividable apparatus for measuring living body impedance in which a first housing section having a first current feeding electrode and a first measurement electrode mounted thereon can physically be separated from a second housing section having a second current feeding electrode and a second measurement electrode mounted thereon, but said first and second housing sections are kept electrically connected to each other via an electric cable. Therefore it is possible to freely set the distance between the electrodes mounted on the first and second housing sections for the measurement. This is effective in that even in case where a person under test is a handicapped person keeping in bed an attendant or assistant person can divide the apparatus into the first and second housing sections and hold them on the parts of the person under test for measurement.

According to an embodiment of the present invention the second housing section is provided with the second current feeding electrode and the second measurement electrode mounted on the same surface thereof. This allows the second housing section to contact with any part of the person for measurement. In particular even in case where a normal person performs the measurement of impedance between one of the hands and any other part of the body there is no need for the person to take unnatural pose such as to bend his body. This assures to produce highly precise measurement result.

According to another embodiment of the present invention the first housing section is provided with the first current feeding electrode and the first measurement electrode mounted on the same surface thereof. In this embodiment the first housing section can be contact with any part of the body for measurement. This allows for the apparatus to handle such case that the measurement of the impedance is limited only to an abdominal region of the person.

According to further embodiment of the present invention the first housing section is provided with the first current feeding electrodes and the first measurement electrodes mounted on a plurality of surfaces thereof. This can make possible for the display unit on the first housing section to be directed toward the person under test within his view field. Therefore the person under test can perform the measurement, while monitoring the progress in measurement.

According to yet further embodiment of the present invention the second housing section is provided with the second current feeding electrodes and the second measurement electrodes mounted on a plurality of surfaces thereof In this embodiment any suitable one of the electrode-mounted surfaces can be selected to suit to the part of the body to be measured.

In addition the present invention provides a guidance information on the display unit for indicating what part of the body is now measured by using names of that part or legend showing that part.

DETAILED DESCRIPTION OF THE PREFERRED EMBODIMENT

Figure 1:
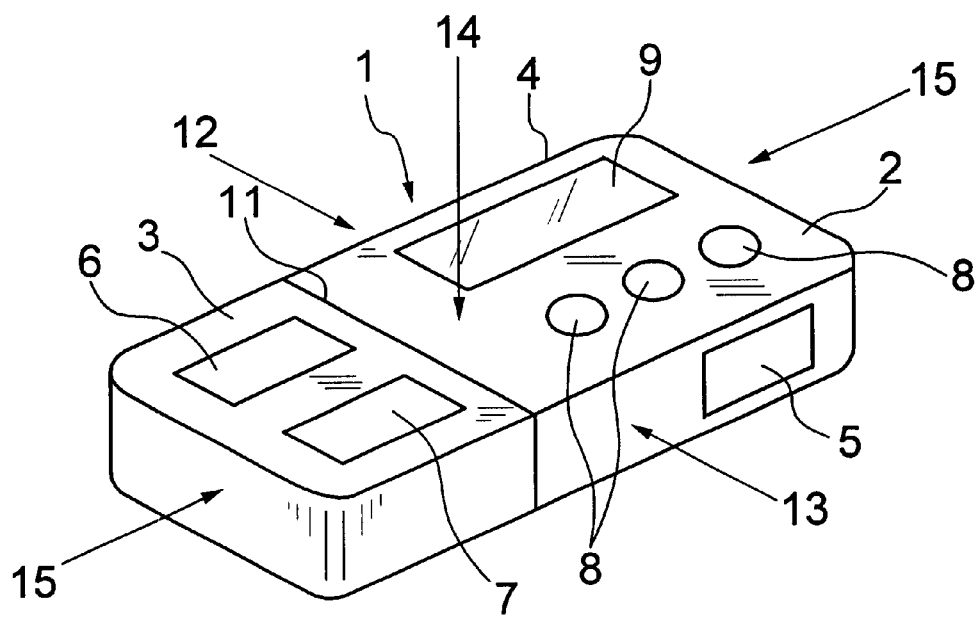
FIG. 1 is a perspective view representing a dividable type body fat measuring apparatus according to an embodiment of the present invention.

According to the present invention a dividable apparatus for measuring living body impedance comprises a first housing section having a first current feeding electrode and a first measurement electrode mounted thereon, and a second housing section. The second housing section includes a second current feeding electrode mounted thereon to establish an electric current path in a living body in relation to said first current feeding electrode. The second housing section further includes a second measurement electrode mounted thereon to detect any potential difference induced in the living body in relation to said first measurement electrode. The first housing section can physically be separated from the second housing section, but they are kept electrically connected to each other via an electric cable. In addition the first housing section includes a measuring unit which measures the impedance based on the potential difference induced in the living body between said first and second measurement electrodes, and a data input unit which sets the measurement condition. The first housing section further includes an arithmetic unit which performs an arithmetic operation based on the data derived by said measuring unit and the data entered by said data input unit, and a display unit which displays the input data and the arithmetic result.

A person under test can divide the measuring apparatus into the first and second housing sections. Then the person grasps the first housing section so that the first current feeding electrode and the first measurement electrode thereon are contact with one part of the body of the person. At the same time the person grasps the second housing section so that the second current feeding electrode and the second measurement electrode thereon are contact with another part of the body of the person. In this condition an electric current path is established between the parts of the body with which the first and second current feeding electrodes are contact. Then any potential difference induced between the parts of the body with which the first and second measurement electrodes are contact is detected to measure the impedance by the measuring unit.

Because of the fact that the apparatus can be divided into two parts or the first and second housing sections, it is possible to freely set the distance between the electrodes mounted on the first and second housing sections. In other words the electrodes can be positioned anywhere on the body of the person for measurement. This is particularly useful in that even a handicapped person keeping in bed can perform the measurement with the help of an attendant or assistant person.

According to an embodiment of the present invention the second housing section is provided with the second current feeding electrode and the second measurement electrode mounted on the same surface thereof. This allows the second housing section separated far from the first housing section and then allows the second housing section to be contact with any part of the body for measurement. Accordingly the person may grasp the first housing section with one of his hands so that the first current feeding electrode and the first measurement electrode thereon are contact therewith. At the same time the person may hold the second housing section so that the second current feeding electrode and the second measurement electrode thereon are contact with another part of the body of the person. In such condition there is no need for the person to take any unnatural pose that adds the burden to him. Therefore higher precision measurement can be assured.

According to another embodiment of the present invention the first housing section is provided with the first current feeding electrode and the first measurement electrode mounted on the same surface thereof. In this embodiment the first housing section can be contact with any part of the body for measurement, instead of the hand, as in the case of the second housing section, as described above. This allows for the first and second housing sections to be positioned anywhere on the body to measure the impedance between any parts of the body.

According to further embodiment of the present invention the first housing section is provided with the first current feeding electrodes and the first measurement electrodes mounted on a plurality of surfaces thereof. In this embodiment the first housing section may be changed in its direction so that the first current feeding electrode and the first measurement electrode thereon are easy to contact with any part of the body. This can make possible for the display unit on the first housing section to be directed toward the person under test within his view field. Therefore the person under test can perform the measurement, while monitoring the progress in measurement.

According to yet further embodiment of the present invention the second housing section is provided with the second current feeding electrodes and the second measurement electrodes mounted on a plurality of surfaces thereof. In this embodiment any suitable one of the electrode-mounted surfaces can be selected to suit to the part of the body to be measured.

In addition the apparatus of the present invention provides a guidance information on the display unit for indicating what part of the body is now measured by using names of that part or legend showing that part. The person under test can clearly confirm what part of the body is measured in advance, and therefore, there is less possibility that he performs the measurement on any wrong part of the body.

As an alternative, for the measurement of impedance between both hands of the person, the first and second housing sections may be kept connected to each other. On the other hand, during the time period the apparatus is not used, to couple the first and second housing sections to each other is convenient for the person to carry the apparatus due to the compactness.

In the above description, the measuring unit, the data input unit and the arithmetic unit have been described as being included in the first housing section. However, some or all of the measuring unit, the data input unit and the arithmetic unit may be included in the second housing section.

Now, a dividable type living impedance measuring apparatus, and more particularly, a dividable type body fat measuring apparatus according to the present invention will be described in detail with reference to the accompanying drawings.

FIG. 1 is a perspective view representing a dividable type body fat measuring apparatus according to an embodiment of the present invention. Referring to this figure, the dividable type body fat measuring apparatus 1 includes a housing formed from a first housing section 2 and a second housing section 3 that are jointed along a seam line 11. The first housing section 2 includes a first current feeding electrode 4 positioned on an upper side surface thereof and a first measurement electrodes 5 positioned on a lower side surface thereof. The first housing section 2 further includes a data input switch 8 for setting measurement condition and a display unit 9 for displaying an input data and an arithmetic result. In addition the first housing section 2 includes a measuring unit for measuring the predetermined impedance on an electronic circuit board mounted therein and an arithmetic unit for performing an arithmetic operation based upon the data fed by the measuring unit and the data entered by the data input switch. The second housing section 3 includes a second current feeding electrode 6 and a second measurement electrode 7 that are positioned on a front surface thereof.

Figure 2:
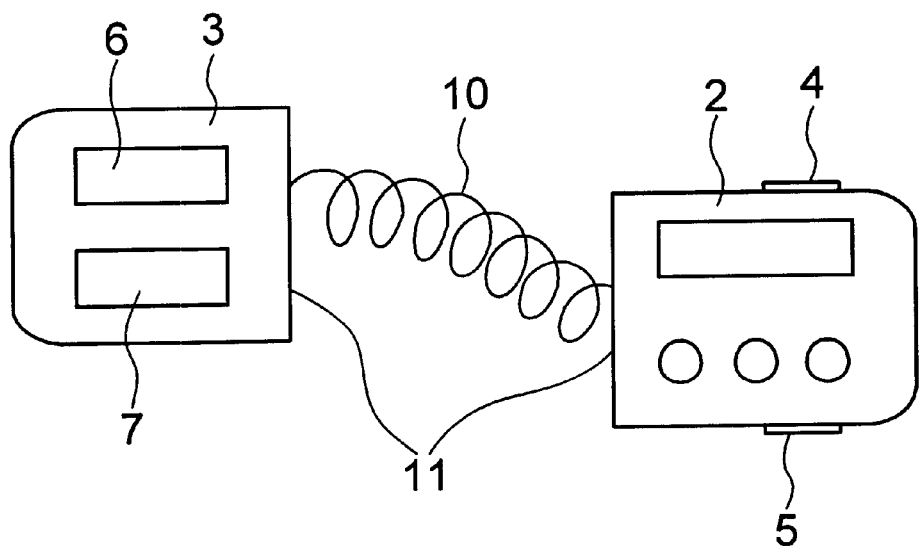
FIG. 2 is a view representing the dividable body fat measuring apparatus in the separated condition.

FIG. 2 is a view representing the dividable body fat measuring apparatus 1 in the divided condition. The first housing sections 2 can physically be separated from the second housing section 3 at the seam line 11. In this condition the both housing section 2 and 3 are kept electrically connected together via an electric cable 10 so that the measurement can be done between the electrodes 4, 5 on the first housing section 2 and the electrodes 6, 7 on the second housing section 3.

Figure 3:
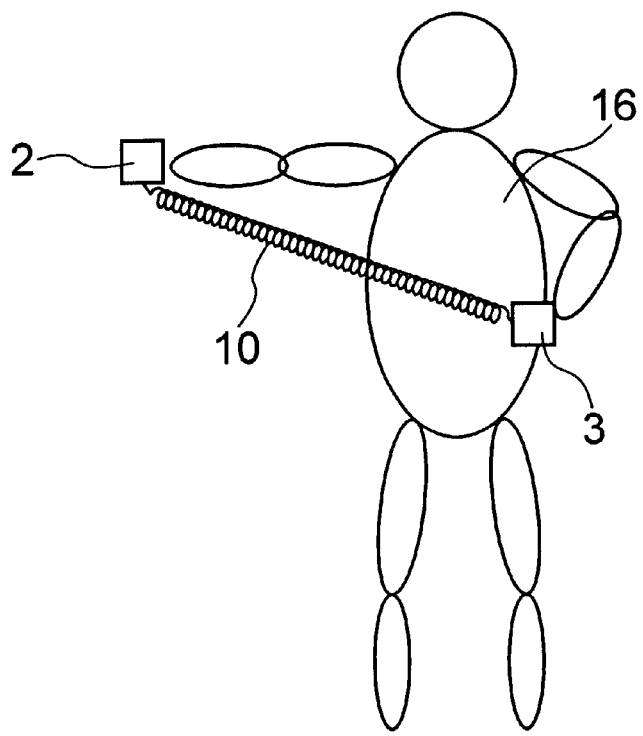
FIG. 3 represents an example case where the measurement is performed between one of the hands and an abdominal region of a person.
Figure 4:
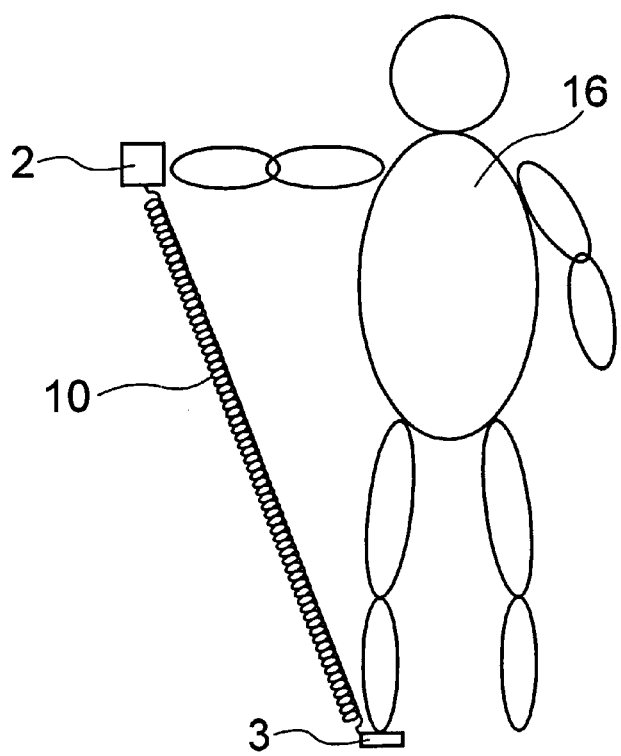
FIG. 4 represents another example case where the measurement is performed between one of the hands and one of the feet of a person.

The measuring operation using the dividable body fat measuring apparatus 1 is performed in the manner as follows: the measuring condition including body weight, body feature, sex, age, height of a person under test, and parts of the body measured is set with the data input switch 8. Then the first housing section 2 is separated from the second housing section 3 at the seam line 11. FIG. 3 represents an example case where the measurement is performed between one of the hands and an abdominal region of a person. FIG. 4 represents another example case where the measurement is performed between one of the hands and one of the feet of a person. Referring to those figures, a person under test grasps the first housing section 2 with one of his hands so that the first current feeding electrode 4 and the first measurement electrode 5 thereon are contact with that hand, while he is standing. At the same time the person under test holds the second housing section 3 so that the second current feeding electrode 6 and the second measurement electrode 7 thereon are contact with his abdomen or his foot. In case where a person under test is a handicapped person keeping in bed, any attendant or assistant person may help to perform the measurement by holding the first and second housing sections 2 and 3 on any parts of the body of the person under test. Accordingly an electric current flows between the first and second current feeding electrodes 4 and 6 so that a current flowing path is established between the hand and the abdomen or foot of the person. Then the potential difference across two points on the current flowing path established between the hand and the abdomen or foot of the person can be detected with the first and second measurement electrodes 5 and 7. Based on the potential difference thus detected, the living body impedance for the person can be derived by means of any prior art measurement unit.

In such manner the first housing section 2 can be separated from the second housing section 3 at the seam line 11 so that they can be selectively disposed at any positions on the body. This means that the measurement distance between the parts of the body to be measured can freely be set. Therefore, even in case of a handicapped person keeping in bed, the measurement can be performed with the help of an assistant person. In addition, because of the same surface (in this case the front surface 14) of the second housing section 3 used for mounting the second current feeding electrode 6 and the second measurement electrode 7, the person under test easily holds those electrodes on any parts of the body (in this case the hand and the abdomen or foot of the person). Therefore the person does not have to take any unnatural pose, such as to bend the body for the measurement, that applies additional burden to the person. This is greatly useful for producing highly precise measurement result.

Figure 5:
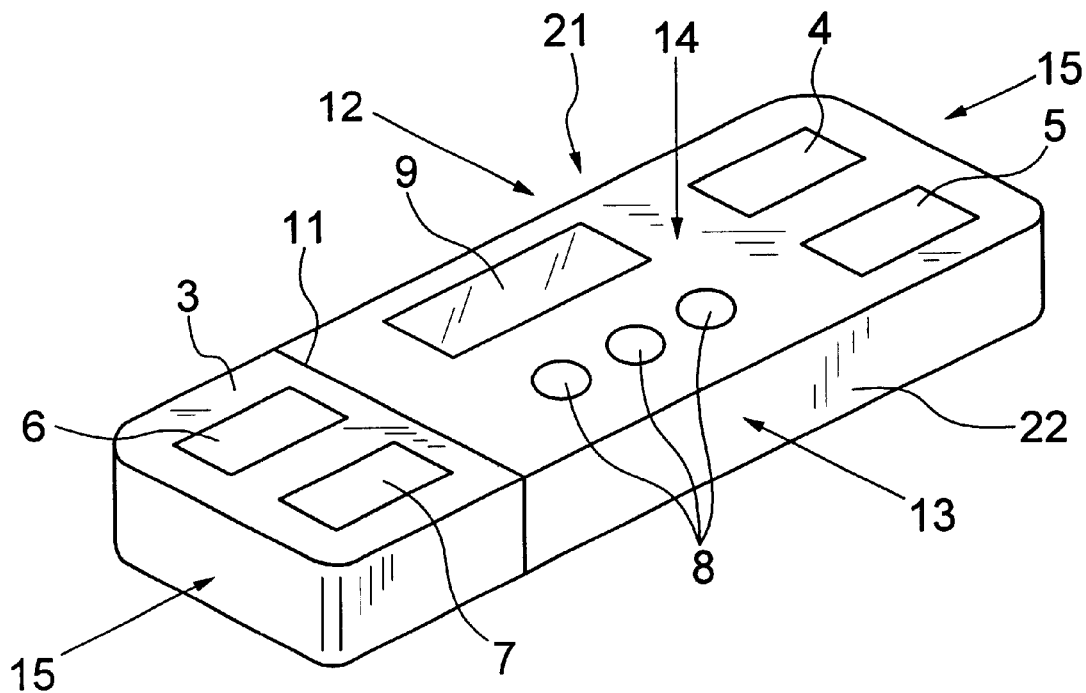
FIG. 5 is a perspective view representing a dividable type body fat measuring apparatus according to another embodiment of the present invention.

FIG. 5 is a perspective view representing a dividable type body fat measuring apparatus according to another embodiment of the present invention. Referring to this figure, the dividable type body fat measuring apparatus 21 includes a housing formed from a first housing section 22 and a second housing section 3 that are jointed along a seam line 11. The first housing section 22 includes a first current feeding electrode 4 and a first measurement electrodes 5 that are positioned on a front surface thereof. The first housing section 22 further includes a data input switch 8 for setting measurement condition and a display unit 9 for displaying an input data and an arithmetic result. In addition the first housing section 22 includes a measuring unit for measuring the predetermined impedance on an electronic circuit board mounted therein and an arithmetic unit for performing an arithmetic operation based upon the data fed by the measuring unit and the data entered by the data input switch. The second housing section 3 includes a second current feeding electrode 6 and a second measurement electrode 7 that are positioned on a front surface thereof.

Figure 6:
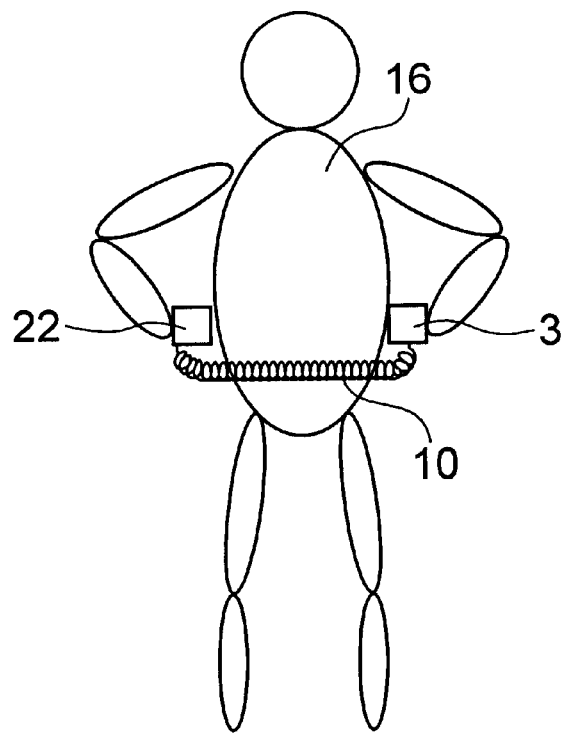
FIG. 6 represents a further example case where the measurement is performed across an abdominal region of a person.

FIG. 6 represents an example case where the measurement is performed between any two positions on an abdominal region of a person using the measuring apparatus in FIG. 5. Referring to this figure, a person under test holds the first housing section 22 so that the first current feeding electrode 4 and the first measurement electrode 5 thereon are contact with the abdomen of the person. At the same time the person under test holds the second housing section 3 so that the second current feeding electrode 6 and the second measurement electrode 7 thereon are contact with the abdomen of the person, but at another position thereon.

In such manner the electrodes on the first and second housing sections 22 and 3 can separately be contact with any selected parts of the body to establish a measurement path therebetween. Therefore it is possible to measure the impedance between any parts of the body other than the abdominal region of the person.

Figure 7:
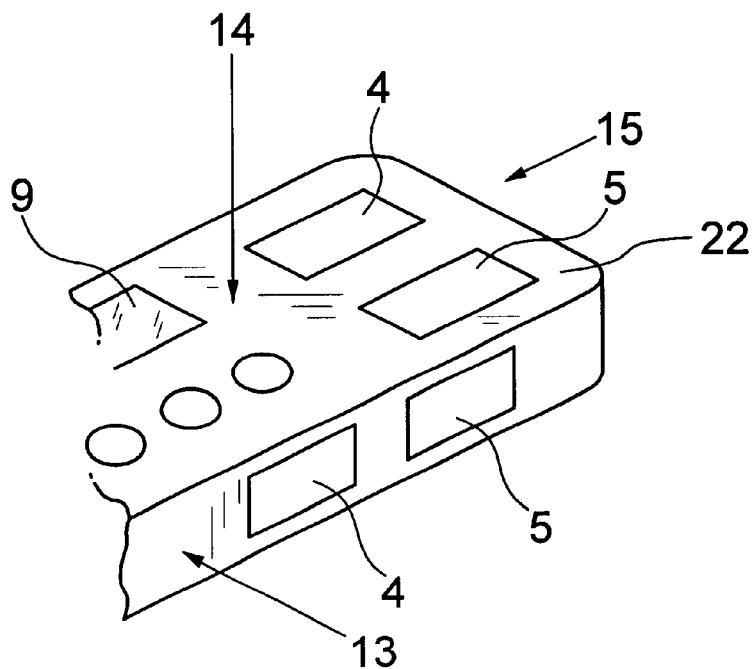
FIG. 7 is a perspective view partly representing a dividable type body fat measuring apparatus according to further embodiment of the present invention.

FIG. 7 is a perspective view partly representing a dividable type body fat measuring apparatus according to further embodiment of the present invention. The measuring apparatus in FIG. 7 includes a first current feeding electrode 4 and a first measurement electrode 5 positioned on a lower side surface 13 of the first housing section 22, which electrodes are provided in addition to the electrodes on the measuring apparatus in FIG. 5. According to this embodiment the first current feeding electrode 4 on the front surface 14 is electrically connected with the first current feeding electrode 4 on the lower side surface 13 within the first housing section 22. In similar manner the first measurement electrode 5 on the front surface 14 is electrically connected with the first measurement electrode 5 on the lower side surface 13.

In this embodiment of the measuring apparatus the first housing section 22 may be changed in its direction so that the first current feeding electrode 4 and the first measurement electrode 5 on the lower side surface 13 are easily contact with the specified part of the body for measurement. At the same time the display unit 9 on the first housing section 22 is easily faced to the person under test within his view field so that the person can perform the measurement operation while monitoring the display unit.

Figure 8:
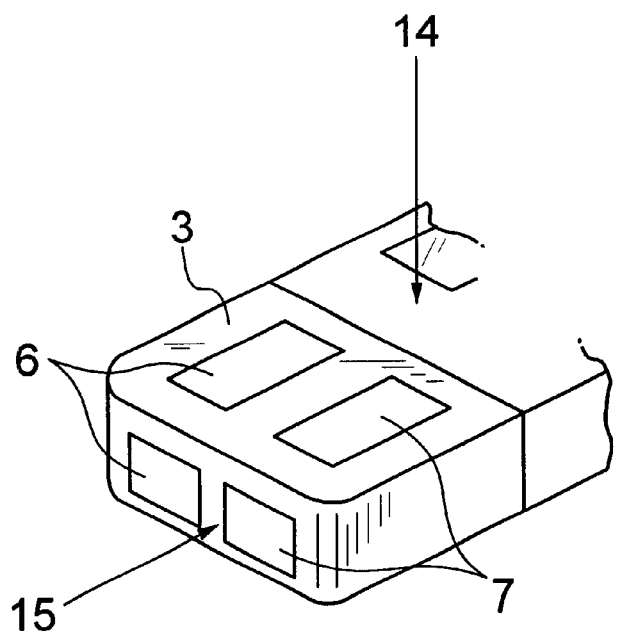
FIG. 8 is a perspective view partly representing a dividable type body fat measuring apparatus according to yet further embodiment of the present invention.

FIG. 8 is a perspective view partly representing a dividable type body fat measuring apparatus according to yet further embodiment of the present invention. In addition to the electrodes on the measuring apparatus in FIGS. 1, 5 and 7, the measuring apparatus in FIG. 8 includes a second current feeding electrode 6 and a second measurement electrode 7 disposed on an end surface 15 of a second housing section 3. According to this embodiment the second current feeding electrode 6 on the front surface 14 is electrically connected with the second current feeding electrode 6 on the end surface 15 within the second housing section 3. In similar manner the second measurement electrode 7 on the front surface 14 is electrically connected with the second measurement electrode 7 on the end surface 15.

In case where the measurement is performed between the hand and the foot, as shown in FIG. 4, the first housing section 2 is held on the hand and the second housing section 3 is held on the foot. In such case it is preferable that the front surface 14 of the second housing section 3 is used as the contact surface for the foot because the person can easily step thereon and keep it in position. Further in case where the measurement is performed across the abdominal region, as shown in FIG. 6, the end surface 15 of the second housing section 3 is preferably used as the contact surface for the abdomen because it is easy to hold the second housing section by the hand. Therefore any suitable one of the electrode-mounted surfaces of the second housing section 3 can be selected to suit to what part of the body is to be measured.

Furthermore, before power up of the measuring apparatus or starting the measurement, names or legend representing all the parts of the body to be measured may be displayed on the display unit 9 and selection of the specified parts of the body may be performed using the switch 8. Thereafter, when performing the measurement, the person under test holds the first and second housing sections 22 and 3 on the parts of the body, according to the information displayed on the display unit 9. In such way there is less possibility to measure wrong parts of the body.

The present invention has been described above with reference to the dividable type body fat measuring apparatus. However, the present invention is not limited to such specific measuring apparatus, but it may be used to any dividable type living impedance measuring apparatus having the electrodes for living impedance measurement, such as a body water measuring device, a pulsimeter, a body composition measuring device, a body fatigue determination unit, an affected part restoration determination unit, and a swell measuring unit.

From the foregoing it is apparent that the present invention provides several advantageous effects as follows:

Because of the dividable housing used the measurement can be performed even by any attendant or assistant person, instead of the person under test himself. There is no need for the person under test to take unnatural pose for the measurement that applies greater burden to the person. This allows the measurement with a stable condition for muscle or fat in the body of the person. Therefore higher precision of the impedance measurement is resulted.

The housing section including the display unit is provided with the electrodes on the same surface thereof. This allows the electrodes to contact with any part of the body for measurement.

Alternatively, the housing section may be provided with the electrodes on a plurality of surfaces thereof. In this case the housing section may be changed in its direction so that the housing section is easy to hold by the person and the measurement is performed while monitoring the display unit thereon.

Furthermore, names or legend representing all the parts of the body to be measured may be displayed on the display unit. This makes easy to confirm the parts of the body to be measured. Then there is less possibility to measure wrong parts of the body.

What is claimed is:

1. A dividable type apparatus for measuring a living body impedance of a living body, comprising:

a first current feeding electrode, a first measurement electrode, a second current feeding electrode, and a second measurement electrode mounted on a housing;

a measuring unit;

a data input unit;

an arithmetic unit; and a display unit;

said housing comprising a first housing section having the first current feeding electrode and the first measurement electrode mounted thereon, said first housing section being of a compact size so that said first housing section can be held by the hand of a user for measurement, and a second housing section couplable to and separable from said first housing section and having the second current feeding electrode and the second measurement electrode mounted thereon, said second housing section being of a compact size so that said second housing section can be held by the hands of the user for measurement, said first and second housing sections being electrically connected to each other via an electric cable;

wherein when said first and second housing sections are coupled to each other, the living body between the first housing section and the second housing section can be measured by holding the coupled first and second housing sections by the hands of the user and making each electrode contact the living body, and when said first and second housing sections are separated from each other, the living body between the separated first and second housing sections can be measured by holding each of the separated first and second housing sections by each of the hands of the user and making each electrode contact the living body;

wherein said second current feeding electrode establishes an electric current path in the living body in relation to said first current feeding electrode, said second measurement electrode detects any potential difference induced in the living body in relation to said first measurement electrode, said measuring unit measures the impedance based on the potential difference induced in the living body between said first and second measurement electrodes, said data input unit sets the measurement condition, said arithmetic unit performs an arithmetic operation based on the data derived by said measuring unit and the data entered by said data input unit, and said display unit displays the input data and the arithmetic result.

2. A dividable type apparatus for measuring living body impedance according to claim 1 in which said second housing section having the second current feeding electrode and the second measurement electrode mounted on the same surface thereof.

3. A dividable type apparatus for measuring living body impedance according to claim 2 in which said first housing section having the first current feeding electrode and the first measurement electrode mounted on the same surface thereof.

4. A dividable type apparatus for measuring living body impedance according to claim 3 in which said first housing section having the first current feeding electrodes and the first measurement electrodes mounted on a plurality of surfaces thereof.

5. A dividable type apparatus for measuring living body impedance according to claim 2, in which said second housing section having the second current feeding electrodes and the second measurement electrodes mounted on a plurality of surfaces thereof.

6. A dividable type apparatus for measuring living body impedance according to claim 1 in which said display unit being operable to display the parts of the living body to be measured.

7. A dividable type apparatus for measuring living body impedance according to any one of claims 2 to 6, wherein said display unit is provided on one surface of said first housing section or on one surface of said second housing section, and said first current feeding electrode and said first measurement electrode or said second current feeding electrode and said second measurement electrode are provided on a single surface of one of said housing sections other than said one surface.

8. A dividable type apparatus for measuring living body impedance according to claim 1, wherein said display unit indicates what part of the living body is measured by using the names of that part or a legend showing that part.

* * * * *